(12) United States Patent
Zheng et al.

(10) Patent No.: US 8,354,668 B2
(45) Date of Patent: Jan. 15, 2013

(54) EMISSIVE TRIARYLS

(75) Inventors: Shijun Zheng, San Diego, CA (US); Jensen Cayas, Bonita, CA (US); Sheng Li, Vista, CA (US); Amane Mochizuchi, San Diego, CA (US); Hyunsik Chae, San Diego, CA (US)

(73) Assignee: Nitto Denko Corporation, Osaka (JP)

( * ) Notice: Subject to any disclaimer, the term of this patent is extended or adjusted under 35 U.S.C. 154(b) by 185 days.

(21) Appl. No.: 12/826,589

(22) Filed: Jun. 29, 2010

(65) Prior Publication Data

US 2010/0327269 A1 Dec. 30, 2010

Related U.S. Application Data

(60) Provisional application No. 61/221,456, filed on Jun. 29, 2009.

(51) Int. Cl.
  *H01L 51/50* (2006.01)
  *C07C 255/50* (2006.01)
  *C07D 209/86* (2006.01)

(52) U.S. Cl. ........... 257/40; 558/424; 548/440; 428/690

(58) Field of Classification Search ................ None
See application file for complete search history.

(56) References Cited

U.S. PATENT DOCUMENTS

| | | | |
|---|---|---|---|
| 3,957,666 A | 5/1976 | Hammann et al. | |
| 5,109,087 A | 4/1992 | Naitoh et al. | |
| 5,417,885 A | 5/1995 | Suzuki et al. | |
| 6,232,322 B1 | 5/2001 | Malamas et al. | |
| 6,359,107 B1 | 3/2002 | Connell et al. | |
| 6,596,350 B2 | 7/2003 | Tarumi et al. | |
| 6,905,741 B2 | 6/2005 | Manabe et al. | |
| 7,314,693 B2 | 1/2008 | Ikegami et al. | |
| 7,373,060 B2 | 5/2008 | Satake et al. | |
| 7,410,997 B2 | 8/2008 | Jinno et al. | |
| 7,425,654 B2 | 9/2008 | Kawamura et al. | |
| 7,851,074 B2 * | 12/2010 | Kido et al. | 428/690 |
| 2004/0127713 A1 | 7/2004 | Jinno et al. | |
| 2007/0190344 A1 | 8/2007 | Inagaki et al. | |
| 2008/0064662 A1 | 3/2008 | Saha et al. | |
| 2009/0008163 A1 | 1/2009 | Chikazawa et al. | |
| 2009/0081636 A1 | 3/2009 | Huang | |
| 2009/0134783 A1 | 5/2009 | Lin et al. | |
| 2010/0060154 A1 | 3/2010 | Nomura et al. | |
| 2010/0308310 A1 | 12/2010 | Zheng et al. | |
| 2010/0308716 A1 | 12/2010 | Zheng | |
| 2010/0326526 A1 | 12/2010 | Zheng | |

FOREIGN PATENT DOCUMENTS

| | | |
|---|---|---|
| DE | 4301700 | 7/1994 |
| EP | 0 499 222 | 2/1992 |
| EP | 0637624 | 2/1995 |
| GB | 1 469 818 A | 4/1977 |

(Continued)

OTHER PUBLICATIONS

English language translation of JP 01009959 A. Feb. 23, 2012.*

(Continued)

*Primary Examiner* — Jennifer Chriss
*Assistant Examiner* — J. L. Yang
(74) *Attorney, Agent, or Firm* — Knobbe Martens Olson & Bear, LLP

(57) ABSTRACT

Disclosed herein are compounds represented by Formula 1. Compositions and light-emitting devices related thereto are also disclosed.

20 Claims, 3 Drawing Sheets

FOREIGN PATENT DOCUMENTS

| | | | |
|---|---|---|---|
| JP | 01009959 A | * | 1/1989 |
| JP | 7-076542 A | | 3/1995 |
| JP | 7138568 | | 5/1995 |
| JP | 7207169 | | 8/1995 |
| JP | 10-340786 A | | 12/1998 |
| JP | 2002-096558 A | | 4/2002 |
| JP | 2011-16798 | | 1/2011 |
| KR | 959189 B1 | | 5/2010 |
| WO | WO 99/58518 A2 | | 11/1999 |
| WO | WO 2004010996 | | 2/2004 |
| WO | WO 2011/008560 | | 1/2011 |

OTHER PUBLICATIONS

CAS Registry No. 168216-32-8 in 1 page, accessed Apr. 23, 2010.
Copending U.S. Appl. No. 12/787,753, filed May 26, 2010.
Copending U.S. Appl. No. 12/788,535, filed May 27, 2010.
Copending U.S. Appl. No. 12/825,953, filed Jun. 29, 2010.
Results of Mar. 30, 2009 search of SureChem-patent_centric database.
Ribierre, Jean-Charles, et al., Effects of Viscoelastic Properties on the Dielectric and Electrooptic Responses of Low-Tg Guest-Host Polymers, Macromolecules 2003, vol. 36, pp. 2516-2525.
Ge, Ziyi et al., "Solution-Processible Bipolar Triphenylamine-Benzimidazole Derivatives for Highly Efficient Single-Layer Organic Light-Emitting Diodes", Chemistry of Materials, Nov. 3, 2008, 20 (7), 2532-2537, XP002608601.
Ge, Ziyi et al., "Spin-Coated Highly Efficient Phosphorescent Organic Light-Emitting Diodes Based on Bipolar Triphenylamine-Benzimidazole Derivatives", Advanced Functional Materials, vol. 18, No. 4, Feb. 22, 2008, pp. 584-590, XP001510816, Wiley, ISSN:1616-301X.
Gustafsson, Flexible light-emitting diodes made from soluble conducting polymer, Nature, vol. 357, pp. 477-479, Jun. 1992.
Kauffman, et al., Synthesis and photophysical properties of fluorescent 2-aryl-1,3-dialkylbenzimidazolium ions and a 1-alkyl-2-arylbenzimidazole with excited state intramolecular proton-transfer. Journal of Heterocyclic Chemistry (1994), 31(4), 957-65.
Kim, et al., Synthesis and properties of highly fluorescent liquid crystals containing bexzoxazole moeity, Gordon and Breach Publishers, No. 337, 1999, pp. 405-408.
Ueda, et al., Synthesis of poly(benzothiazole)s by direct polycondensation of dicarboxylic acids with 2,5-diamino-1, 4-benzenedithiol dihydrochloride using phosphorus pentoxide/ methaneusulfonic acid as condensing agent and solvent, Polymer Journal vol. 18, No. 2, 1986 pp. 117-122.
CIE 1971, International Commission on Illumination, Colorimetry: Official Recommendations of the International Commission on Illumination, Publication CIE No. 15 (E-1.3.1) 1971, Bureau Central de la CIE, Paris, 1971.

* cited by examiner

EMISSIVE TRIARYLS

CROSS-REFERENCE TO RELATED APPLICATIONS

This application claims the benefit of U.S. Provisional Application No. 61/221,456, filed Jun. 29, 2009, which is incorporated by reference herein in its entirety.

BACKGROUND

1. Field of the Invention

This invention relates to light-emitting compounds or compositions and light-emitting devices that include the light-emitting compounds or compositions.

2. Description of the Related Art

Organic light-emitting devices (OLEDs) have been widely developed for flat panel displays, and are moving fast towards solid state lighting (SSL) applications. Organic Light Emitting Diodes (OLEDs) include a cathode, an emissive layer and an anode, and typically further include a hole transporting layer and an electron transporting layer. Light emitted from an OLED device is the result of recombination of positive charges (holes) and negative charges (electrons) inside an organic (emissive) layer. The holes and electrons combine within a single molecule or a small cluster of molecules to generate excitons, which are molecules in an excited state, or groups of organic molecules bound together in an excited state. When an exciton releases the required energy and returns to its stable state, photons are generated. The organic compound or group of compounds which forms excitons and emits photons is referred as an electro-fluorescent material or electro-phosphorescent material depending on the nature of the radiative process. Thus the OLED emissive compounds may be selected for their ability to absorb primary radiation and emit radiation of a desired wavelength. For blue emitters, for example, emission within principle emission bands of 440 to 490 nm is desirable.

Some SSL applications require white OLED devices to achieve greater than 1,500 lm brightness, a color rendering index (CRI) greater than 70, and an operating time greater than 100,000 hours at 1,000 lm/w. There are many approaches for generating white light from an OLED, but two common approaches are: direct combination of red, blue, and green light using either lateral patterning or vertical stacking of three emitters; and partial down conversion of blue light in combination with yellow phosphors. Both of these common approaches may be more effective if a highly efficient chemical- and photo-stable blue dye is employed. However, blue emitters may be less stable than dyes which emit other colors. Furthermore, there are very few blue emitting devices showing a CIE y value below about 0.2 yet while maintaining respectable efficiency. Thus, the development of deep blue emitters with good stability and high luminescence efficiency is desirable to effectively reduce power consumption and generate emission of different colors.

Certain triphenyl compounds have been used as additives in organic photoreflective polymer composites for electrooptic, photorefractive and liquid crystal applications (see for example, JP 07138568). However, none of these compounds were described as blue emitting fluorescent compounds. Thus, the development of deep blue emitters with good stability and high luminescence efficiency is desirable to effectively reduce power consumption and generate emission of different colors.

SUMMARY OF THE INVENTION

Some embodiments provide compounds that are useful as deep blue emitters. Some embodiments provide compounds which may be useful as a deep blue emitter which comprises a series of 2, 3, or 4 directly connected aryl rings, such as 3 or 4 directly connected optionally substituted phenyl or interphenylene rings; wherein 2 of the aryl rings are a first terminal aryl ring comprising at least one electron donating substituent and a second terminal aryl ring comprising at least one electron withdrawing substituent; wherein the first terminal aryl ring and the second terminal aryl ring are optionally bridged by the remaining optionally substituted rings.

Some embodiments provide compounds represented by Formula 1:

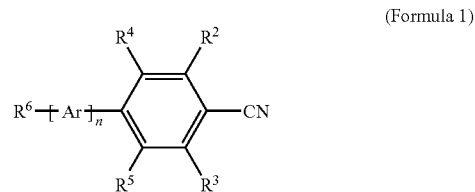

(Formula 1)

wherein $R^2$ and $R^3$ are independently F, Cl, or $C_{1-12}$ perfluoroalkyl; $R^4$ and $R^5$ are independently H, F, Cl, or $C_{1-10}$ alkyl; each Ar is independently 1,4-interarylene having 0, 1, or 2 substituents independently selected from $C_{1-3}$ alkyl, F, and Cl; n is 0, 1, 2, or 3, $R^6$ is an optionally substituted diarylamino, optionally substituted diarylaminophenoxy, or $R^7$—O-Ph-O—; Ph is optionally substituted p-interphenylene; and $R^7$ is $C_{1-10}$ alkyl or $C_{1-9}O_{1-4}$ ether.

Some embodiments provide a light-emitting device comprising: an anode layer; a cathode layer; and a light-emitting layer positioned between, and electrically connected to, the anode layer and the cathode layer, the light-emitting layer comprising a compound disclosed herein.

These and other embodiments are described in greater detail below.

DETAILED DESCRIPTION

Figure 1:
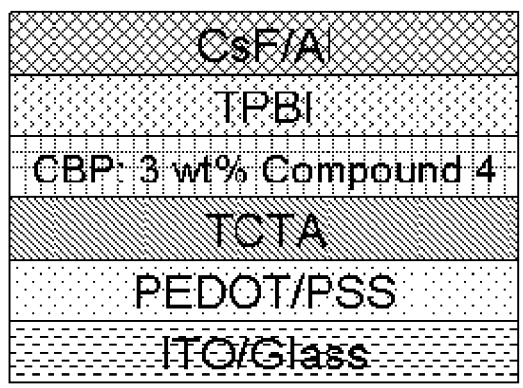
FIG. 1 shows an exemplary configuration of an embodiment of an organic light-emitting device incorporating a compound disclosed herein.

Reference to a compound herein also includes any salts of that compound.

Unless otherwise indicated, when a structural feature such as alkyl or aryl is referred to as being "optionally substituted," it is meant that the feature may have no substituents or may have one or more substituents. A structural feature that is "substituted" has one or more substituents. The term "substituent" has the ordinary meaning known to one of ordinary skill in the art. In some embodiments, the substituent is a halogen, or is a $C_{1-20}$ hydrocarbon, or is a $C_{1-20}$ heterohydrocarbon moiety, meaning a hydrocarbon moiety having from 1-10 heteroatom replacements, wherein the heteroatom replacements are selected from: 1) replacing a C with N+ (e.g. $CH_2NH_3^+$ instead of $CH_2CH_3$), 2) replacing a CH with N (e.g. —$NHCH_3$ instead of —$CH_2CH_3$ or C≡NH instead of C═$CH_2$), 3) replacing a $CH_2$ with O, S, or $SO_2$ (e.g. $CH_2OCH_3$ instead of $CH_2CH_2CH_3$ or C═O instead of C═$CH_2$, or 4) replacing H with a halogen or —$NO_2$ (e.g. $CH_2F$ instead of $CH_3$). In other embodiments, the substituent has from 1-20 carbon atoms and from 0-10 heteroatoms independently selected from: N, O, S, F, Cl, Br, I, and combinations thereof. In some embodiments, the substituent has at least 1 carbon atom or at least 1 heteroatom, and has from 0-10 carbon atoms and from 0-5 heteroatoms independently selected from: N, O, S, F, Cl, Br, I, and combinations thereof. Examples of substituents include, but are not limited to, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxyl, aryloxy, acyl, ester, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, —CNO, —NCO, thiocyanato, isothiocyanato, nitro, silyl, sulfenyl, sulfinyl, sulfonyl, haloalkyl, haloalkoxyl, trihalomethanesulfonyl, trihalomethanesulfonamido, and amino, including mono- and di-substituted amino groups, and the protected derivatives thereof.

The term "electron-donating substituent" has the ordinary meaning known to one of ordinary skill in the art. In some embodiments, the electron-donating substituent has from 1-20 carbon atoms, from 1-10 carbon atoms, or has a molecular weight of less than about 500, 300, or 200. In some embodiments, the substituent has at least 1 carbon atom or at least 1 heteroatom, and has from 0-10 carbon atoms and from 0-5 heteroatoms independently selected from: N, O, S and combinations thereof. In some embodiments, the electron-donating substituent is an electron donor with respect to a phenyl ring to which it is attached. Some examples of electron-donating substituents may include, but are not limited to: alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxyl, aryloxy, O-ester, mercapto, alkylthio, arylthio, O-carbamyl, N-carbamyl, O-thiocarbamyl, N-thiocarbamyl, N-amido, O-carboxy, silyl, and amino.

The term "electron-withdrawing substituent" has the ordinary meaning known to one of ordinary skill in the art. In some embodiments, the electron-withdrawing substituent is a halogen, or has from 1-20 carbon atoms, from 1-10 carbon atoms, or has a molecular weight of less than about 500, 300, or 200. In some embodiments, the substituent has at least 1 carbon atom or at least 1 heteroatom, and has from 0-10 carbon atoms and from 0-5 heteroatoms independently selected from: N, O, S, F, Cl and combinations thereof. In some embodiments, the electron-withdrawing substituent is electron withdrawing with respect to a phenyl ring to which it is attached. Some examples of electron-withdrawing substituents may include, but are not limited to: acyl, C-ester, cyano, halogen, carbonyl, C-amido, thiocarbonyl, C-carboxy, protected C-carboxy, isocyanato, thiocyanato, isothiocyanato, nitro, sulfinyl, sulfonyl, perflouoralkyl, trihalomethanesulfonyl, and trihalomethanesulfonamido.

The term "aryl" as used herein refers to an aromatic ring or ring system. Exemplary aryl groups are phenyl, naphthyl, etc. The designations "$C_{6-30}$ aryl" and "$C_6$-$C_{30}$ aryl" refer to an aryl where the ring or ring system has from 6-30 carbon atoms, and do not characterize or limit any substituents attached to the ring atoms. Similar designations refer to aryl with a number of carbon atoms in a different range.

The term "heteroaryl" as used herein refers to an aromatic ring or ring system having one or more atoms selected from nitrogen, oxygen, or sulfur in an aromatic ring. Examples include pyridinyl, pyridazinyl, triazinyl, pyridinyl, pyrimidinyl, pyrazinyl, benzoimidazolyl, indolyl, benzooxazolyl, carbazolyl, etc. The designation "$C_{3-30}$ heteroaryl" refers to heteroaryl where the ring or ring system has from 3-30 carbon atoms, and one or more atoms selected from nitrogen, oxygen or sulfur in a ring or ring system, and does not characterize or limit any hydrogen or substituents attached to the ring atoms. Similar designations refer to heteroaryl with a number of carbon atoms in a different range.

The term "alkyl" as used herein refers to a moiety consisting of carbon and hydrogen containing no double or triple bonds. Alkyl may be linear, branched, cyclic, or a combination thereof, and may contain from one to thirty-five carbon atoms. Examples of alkyl groups include but are not limited to methyl, ethyl, propyl, isopropyl, cyclopropyl, butyl isomers (e.g. n-butyl, iso-butyl, tert-butyl, etc.) cyclobutyl isomers (e.g. cyclobutyl, methylcyclopropyl, etc.), pentyl isomers, cyclopentane isomers, hexyl isomers, cyclohexane isomers, and the like. The term "linear alkyl" refers to —$(CH_2)_qCH_3$, where q is 0-34. The designation "$C_{1-30}$ alkyl" or a similar designation, refers to alkyl having from 1 to 30 carbon atoms such as methyl, ethyl, propyl isomers (e.g. n-propyl, isopropyl, etc.), butyl isomers, cyclobutyl isomers (e.g. cyclobutyl, methylcyclopropyl, etc.), pentyl isomers, cyclopentyl isomers, hexyl isomers, cyclohexyl isomer, heptyl isomers, cycloheptyl isomers, octyl isomers, cyclooctyl isomers, nonyl isomers, cyclononyl isomers, decyl isomer, cyclodecyl isomers, etc. Similar designations refer to alkyl with a number of carbon atoms in a different range.

The term "perfluoroalkyl" as used herein refers to alkyl wherein all hydrogens are replaced by fluorine, such as —$CF_3$, —$C_2F_5$, etc. The designation "$C_{1-12}$ perfluoroalkyl" or a similar designation, refers to perfluoroalkyl having from 1 to 12 carbon atoms such as perfluoromethyl, perfluoroethyl, perfluoropropyl isomers, perfluorocyclopropyl, perfluorobutyl isomers, perfluorocyclobutyl isomers, perfluoropentyl isomers, perfluorocyclopentyl isomers, perfluorohexyl isomers, perfluorocyclohexyl isomers, perfluoroheptyl isomers, perfluorocycloheptyl isomers, etc. Similar designations refer to perfluoroalkyl with a number of carbon atoms in a different range.

The term "ether" as used herein refers to a moiety comprising carbon, hydrogen, and single bonded oxygen, i.e. —O—, provided that —O—O— is not present. A person of ordinary skill in the art understands that when a moiety such as $R^7$ is an ether (such as a $C_{1-9}O_{1-4}$ ether) which is directly attached to an oxygen atom (e.g. $R^7$—O-Ph-O—), a carbon atom of the ether attaches to the oxygen atom so that —O—O— is excluded (e.g. —O—O—C≡C-D would be excluded). Examples include: alkoxy (—O-alkyl), such as —O-methyl, —O-ethyl, —O-propyl, —O-isopropyl, etc.; -alkyl-O-alkyl, such as -methyl-O-methyl, -methyl-O-ethyl, -methyl-O-isopropyl, etc.; and —$(CH_2CH_2O)_n$—. The designation "$C_{1-30}O_{1-15}$ ether" or a similar designation refers to ether having from 1-30 carbon atoms, from 1-15 oxygen atoms, and hydrogen. Examples include, but are not limited to, —$(CH_2CH_2O)_nCH_3$— where n is 1, 2, 3, 4, 5, 6, 7, 8, 9, 10, 11, 12, 13, or 14; —$[CH(CH_3)CH_2O]_nCH_3$— where n is 1, 2, 3, 4, 5, 6, 7, 8, or 9; —$(CH_2)_o$—O—$(CH_2)_pCH_3$ where o+p is from 1-29; etc.

The term "interarylene" as used herein, is a subgenus of "aryl," and refers to aryl which attaches at two different positions. For "1,4-interarylene," a subsgenus of "interarylene," the two positions are "1,4-," which refers to the first and fourth atom of a series of four (4) consecutive atoms of a ring. Examples of "1,4-interarylene" include, but are not limited to:

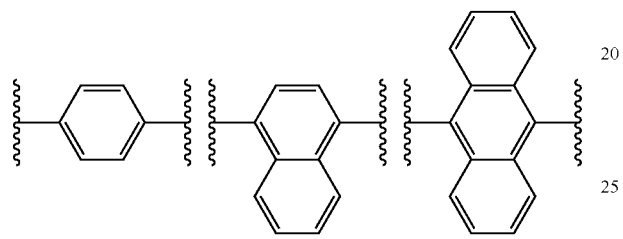

The term "p-interphenylene" as used herein, is a subgenus of "phenyl" and a subgenus of "1,4-interarylene" and refers to:

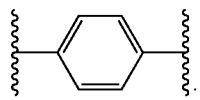

The term "diarylamino" as used herein refers to a nitrogen atom which is attached to two independent aryl rings. In some embodiments, the aryl rings may have one or more bonds between them such that a fused ring system is formed which may incorporate the nitrogen. In some embodiments, one or both of the aryl rings may also have one or more bonds to an aryl ring to which the nitrogen is attached such that a fused ring system is formed which may incorporate the nitrogen. Some non-limiting examples of "diarylamino" include carbazol-9-yl and diphenylamino, which are shown below.

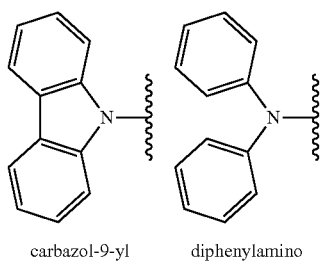

carbazol-9-yl    diphenylamino

The term "diarylaminophenoxy" as used herein refers to a phenoxy (e.g. —O-Phenyl) moiety which carries a diarylamino substituent. In some embodiments, one or more of the phenoxy ring and the two aryl rings may be connected by one or more double bonds. Some non-limiting examples of "diarylaminophenoxy" are shown below.

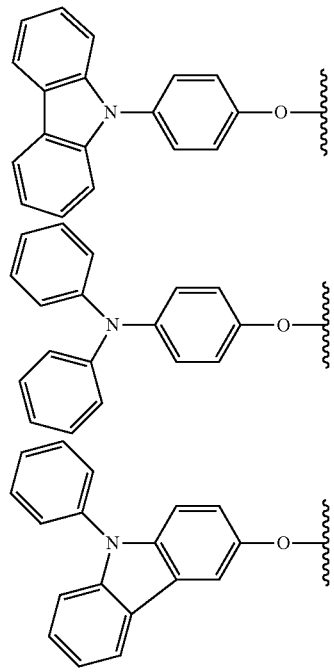

The term "work function" as used herein in referring to a metal is a measure of the minimum energy required to extract an electron from the surface of the metal.

The term "high work function metal" as used herein refers to a metal or alloy that easily injects holes and typically has a work function of at least about 4.5.

The term "low work function metal" as used herein refers to a metal or alloy that easily loses electrons and typically has a work function less than about 4.3.

A material is white light-emitting if it emits white light. White light is light having the approximate CIE color coordinates (X=1/3, Y=1/3). The CIE color coordinates (X=1/3, Y=1/3) is defined as the achromatic point. The X and Y color coordinates are weights applied to the CIE primaries to match a color. A more detailed description of these terms may be found in CIE 1971, International Commission on Illumination, Colorimetry: Official Recommendations of the International Commission on Illumination, Publication CIE No. 15 (E-1.3.1) 1971, Bureau Central de la CEE, Paris, 1971 and in F. W. Billmeyer, Jr., M. Saltzman, Principles of Color Technology, 2nd edition, John Wiley & Sons, Inc., New York, 1981, both of which are hereby incorporated by reference in their entireties. The color rendering index (CRI) refers to the ability to render various colors and has values ranging from 0 to 100, with 100 being the best.

A material is "deep blue" emitting if it emits deep blue light. Deep blue light is light having the approximate CIE color coordinates (X<0.2 and Y<0.1). A non-limiting example is (X=[0.14], Y=[0.08], CIE 1931).

Some embodiments provide a compound which may be useful as a deep blue emitter, which compound comprises a series of 2, 3, or 4 directly connected aryl rings, such as 3 or 4 directly connected optionally substituted phenyl or interphenylene rings; wherein 2 of the aryl rings are a first terminal aryl ring comprising at least one electron donating substituent and a second terminal aryl ring comprising at least one electron withdrawing substituent; wherein the first terminal aryl ring and the second terminal aryl ring are optionally bridged by the remaining optionally substituted interarylene rings, optionally along with other bridging atoms.

In some embodiments, the electron withdrawing substituent is at a m- or a p-position with respect to the optionally substituted interarylene or interphenylene ring to which it attaches. In some embodiments, the electron donating substitutent comprises an optionally substituted phenoxy or an optionally substituted diarylamino at a p-position with respect to the optionally substituted interarylene or interphenylene ring to which it attaches.

While not being limited by any particular theory or mechanism, it is believed that constructing the blue emitting compound to have a "push" (electron donating) end and a "pull" (electron-withdrawing or electron-accepting) end may affect the orbital structure of an emissive molecule to the extent that the energy levels of the molecule may shift from an ultraviolet emitting compound to a deep blue emitting compound.

Thus, in an embodiment, a terminal phenyl at the "push" end of a blue emitting compound comprises at least one substituent with an electron donating hetero-atom, e.g., N, O or S. In another embodiment, a terminal phenyl at the "push" end comprises at least one electron donating substituent in at least one of the m- and/or p-positions with respect to the interarylene to which it attaches. In some embodiments, the electron donating group may be a methyl group, an isopropyl group, a phenoxy group, a benzyloxy group, a dimethylamino group, a diphenylamino group, a pyrrolidine group, or a phenyl group, In some embodiments, a terminal phenyl at the "pull" end of a deep blue emitting compound can independently comprise at least one electron withdrawing substituent, such as at least one of a fluoro group, a cyano group, a trifluoromethyl group, or a phenyl group with a trifluoromethyl moiety. Some compounds of Formula 1 may be examples of these "push-pull" systems.

With respect to compounds of Formula 1, $R^2$ and $R^3$ may be independently F, Cl, or $C_{1-12}$ perfluoroalkyl (e.g. linear or branched perfluoroalkyl such as: $CF_3$, $C_2F_5$, $C_3F_7$, $C_4F_9$, $C_5F_{11}$, $C_6F_{13}$, $C_7F_{15}$, $C_8F_{17}$, etc., or cyclic perfluoroalkyl such as: $C_3F_6$, $C_4F_8$, $C_5F_{10}$, $C_6F_{12}$, $C_7F_{14}$, $C_8F_{16}$, etc). In some embodiments, $R^2$ and $R^3$ are independently F or Cl.

$R^4$ and $R^5$ may be independently H, F, Cl, or $C_{1-10}$ alkyl (e.g. linear or branched alkyl such as: $CH_3$, $C_2H_5$, $C_3H_7$, $C_4H_9$, $C_5H_{11}$, $C_6H_{13}$, $C_7H_{15}$, $C_8H_{17}$, etc., cycloalkyl such as: $C_3H_6$, $C_4H_8$, $C_5H_{10}$, $C_6H_{12}$, $C_7H_{14}$, $C_8H_{16}$, etc.).

Each Ar may independently be 1,4-arylene (such as p-interphenylene, 1,4-internapthylene, etc.) having 0, 1, or 2, substituents independently selected from $C_{1-3}$ alkyl (e.g. $CH_3$, $C_2H_5$, $C_3H_7$, cyclopropyl, etc.), F, and Cl. In some embodiments, at least 1 Ar is unsubstituted.

In some embodiments, n is 2.

$R^6$ may be optionally substituted diarylamino (such as diphenylamino or carbazolyl, wherein each phenyl of the diphenylamino or carbazolyl may independently have 0, 1, 2, or 3 substituents independently selected from $C_{1-6}$ alkyl, $C_{1-6}$ ether, or $-NR'_2$, wherein each R' is independently H, $C_{1-6}$ alkyl, or optionally substituted aryl, etc.); diarylaminophenoxy (such as diphenylaminophenoxy or carbazolylphenoxy, wherein each phenyl of the diphenylaminophenoxy or carbazolylphenoxy may independently have 0, 1, 2, or 3 substituents independently selected from $C_{1-6}$ alkyl, $C_{1-6}$ ether, $-NR'_2$, and optionally substituted aryl, etc.); or $R^7$—O—Ph-O— wherein Ph is optionally substituted p-interphenylene (which may have substituents such as $C_{1-6}$ alkyl, $C_{1-6}$ ether, or $-NR'_2$) and $R^7$ is $C_{1-10}$ alkyl (e.g. linear or branched $CH_3$, $C_2H_5$, $C_3H_7$, $C_4H_9$, $C_5H_{11}$, $C_6H_{13}$, $C_7H_{15}$, etc., cyclic $C_3H_6$, $C_4H_8$, $C_5H_{10}$, $C_6H_{12}$, etc.) or $C_{1-9}O_{1-4}$ ether (e.g. $C_{1-9}$ alkoxy, such as methoxy, ethoxy, propoxy isomers, butoxy isomers, pentoxy isomers, hexoxy isomers, heptoxy isomers, etc., alkylene oxides such as $-(CHR''CHR''O)_oH$, wherein o is 1, 2, 3, or 4, and each R" is independently H or $C_{1-2}$ alkyl, including hydroxyethyl, diethylene oxide (i.e. both R" are H and o is 2), triethylene oxide (i.e. both R" are H and o is 3), etc.).

In some embodiments, $R^6$ is:

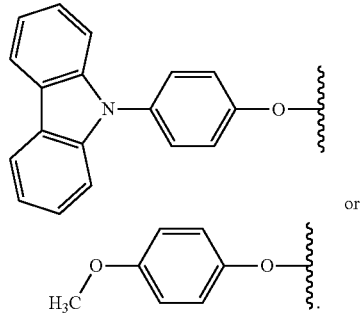

or

In some embodiments, the compound is further represented by Formula 2 or Formula 3:

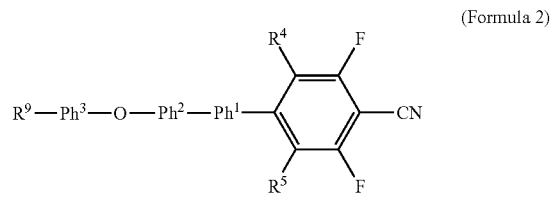

(Formula 2)

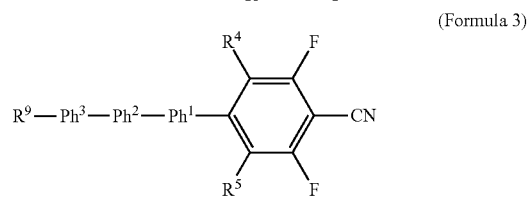

(Formula 3)

wherein $Ph^1$, $Ph^2$, and $Ph^3$ are independently optionally substituted p-interphenylene and $R^9$ is $O-R^7$ or optionally substituted carbazol-9-yl. In some embodiments, $Ph^1$, $Ph^2$, and $Ph^3$ independently have 0, 1, or 2 substituents independently selected from $C_{1-3}$ alkyl (e.g. methyl, ethyl, propyl isomers, cyclopropyl, etc.), F, and Cl.

Some non-limiting examples of useful compounds include:

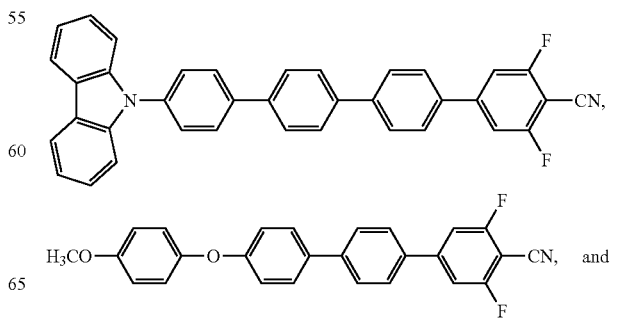

and

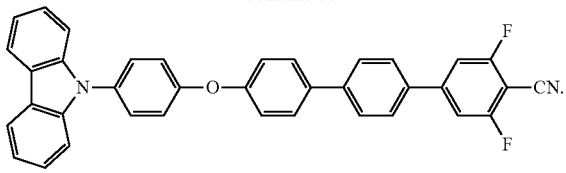

The compounds and compositions described herein can be incorporated into light-emitting devices in various ways. For example, an embodiment provides a light-emitting device comprising: an anode layer (e.g., an anode layer comprising a high work function metal); a cathode layer (e.g., a cathode layer comprising a low work function metal); and a light-emitting layer positioned between, and electrically connected to, the anode layer and the cathode layer. The light-emitting layer comprises the compounds and/or compositions disclosed herein.

The anode layer may comprise a conventional material such as a metal, mixed metal, alloy, metal oxide or mixed-metal oxide, conductive polymer, and/or an inorganic material such as carbon nanotube (CNT). Examples of suitable metals include the Group 1 metals, the metals in Groups 4, 5, 6, and the Group 8-10 transition metals. If the anode layer is to be light-transmitting, metals in Group 10 and 11, such as Au, Pt, and Ag or alloys thereof, or mixed-metal oxides of Group 12, 13, and 14 metals, such as indium-tin-oxide (ITO), indium-zinc-oxide (IZO), and the like, may be used. In some embodiments, the anode layer may be an organic material such as polyaniline. The use of polyaniline is described in "Flexible light-emitting diodes made from soluble conducting polymer," Nature, vol. 357, pp. 477-479 (11 Jun. 1992). Examples of suitable high work function metals and metal oxides include but are not limited to Au, Pt, or alloys thereof, ITO, IZO, and the like. In some embodiments, the anode layer can have a thickness in the range of about 1 nm to about 1000 nm.

A cathode layer may include a material having a lower work function than the anode layer. Examples of suitable materials for the cathode layer include those selected from alkali metals of Group 1, Group 2 metals, Group 12 metals including rare earth elements, lanthanides and actinides, materials such as aluminum, indium, calcium, barium, samarium and magnesium, and combinations thereof. Li-containing organometallic compounds, LiF, and $Li_2O$ may also be deposited between the organic layer and the cathode layer to lower the operating voltage. Suitable low work function metals include but are not limited to Al, Ag, Mg, Ca, Cu, Mg/Ag, LiF/Al, CsF, CsF/Al or alloys thereof. In an embodiment, the cathode layer can have a thickness in the range of about 1 nm to about 1000 nm.

The amount of the compounds disclosed herein in the light-emitting composition can vary. In some embodiments, the light-emitting layer consists essentially of a compound disclosed herein. In other embodiments, the emissive layer comprises a host material and at least one of the emissive compounds disclosed herein. If there is a host material, the amount of the emissive compound with respect to the host material may be any amount suitable to produce adequate emission. In some embodiments, the amount of a compound disclosed herein in the light-emitting layer is in the range of from about 1% to about 100% by weight of the light-emitting layer, about 1% to about 10%, or alternatively, about 3% by weight of the light-emitting layer.

The thickness of the light-emitting layer may vary. In one embodiment, the light-emitting layer has a thickness in the range of from about 20 nm to about 150 nm, or from about 20 nm to about 200 nm.

The host in the emissive layer may be at least one of: one or more hole-transport materials, one or more electron-transport materials, and one or more ambipolar materials, which are materials understood by those skilled in the art to be capable of transporting both holes and electrons.

In some embodiments, the hole-transport material comprises at least one of an aromatic-substituted amine, a carbazole, a polyvinylcarbazole (PVK), e.g. poly(9-vinylcarbazole); N,N'-bis(3-methylphenyl)N,N'-diphenyl-[1,1'-biphenyl]-4,4'-diamine (TPD); polyfluorene; a polyfluorene copolymer; poly(9,9-di-n-octylfluorene-alt-benzothiadiazole); poly(paraphenylene); poly[2-(5-cyano-5-methylhexyloxy)-1,4-phenylene]; 1,1-Bis(4-bis(4-methylphenyl)aminophenyl)cyclohexane; 2,9-Dimethyl-4,7-diphenyl-1,10-phenanthroline; 3,5-Bis(4-tert-butyl-phenyl)-4-phenyl[1,2,4]triazole; 3,4,5-Triphenyl-1,2,3-triazole; 4,4',4"-Tris(N-(naphthylen-2-yl)-N-phenylamino)triphenylamine; 4,4',4'-tris(3-methylphenylphenylamino)triphenylamine (MTDATA); 4,4'-bis[N-(naphthyl)-N-phenyl-amino]biphenyl (α-NPD); 4,4'-bis[N,N'-(3-tolyl)amino]-3,3'-dimethylbiphenyl (HMTPD); 4,4'-N,N'-dicarbazole-biphenyl (CBP); 1,3-N,N-dicarbazole-benzene (mCP); poly(9-vinylcarbazole) (PVK); a benzidine; a phenylenediamine; a phthalocyanine metal complex; a polyacetylene; a polythiophene; a triphenylamine; an oxadiazole; copper phthalocyanine; N,N'N"-1,3,5-tricarbazoloylbenzene (tCP); N,N'-bis(4-butylphenyl)-N,N'-bis(phenyl)benzidine; mixtures thereof, and the like.

In some embodiments, the electron-transport material comprises at least one of 2-(4-biphenylyl)-5-(4-tert-butylphenyl)-1,3,4-oxadiazole (PBD); 1,3-bis(N,N-t-butyl-phenyl)-1,3,4-oxadiazole (OXD-7), 1,3-bis[2-(2,2'-bipyridine-6-yl)-1,3,4-oxadiazo-5-yl]benzene; 3-phenyl-4-(1'-naphthyl)-5-phenyl-1,2,4-triazole (TAZ); 2,9-dimethyl-4,7-diphenyl-phenanthroline (bathocuproine or BCP); aluminum tris(8-hydroxyquinolate) (Alq3); and 1,3,5-tris(2-N-phenylbenzimidazolyl)benzene; 1,3-bis[2-(2,2'-bipyridine-6-yl)-1,3,4-oxadiazo-5-yl]benzene (BPY-OXD); 3-phenyl-4-(1'-naphthyl)-5-phenyl-1,2,4-triazole (TAZ), 2,9-dimethyl-4,7-diphenyl-phenanthroline (bathocuproine or BCP); and 1,3,5-tris[2-N-phenylbenzimidazol-z-yl]benzene (TPBI). In one embodiment, the electron transport layer is aluminum quinolate ($Alq_3$), 2-(4-biphenylyl)-5-(4-tert-butylphenyl)-1,3,4-oxadiazole (PBD), phenanthroline, quinoxaline, 1,3,5-tris [N-phenylbenzimidazol-z-yl]benzene (TPBI), or a derivative or a mixture thereof.

In some embodiments, the device comprises no electron transport or hole transport layer. In some embodiments, the device consists essentially of the anode layer, the cathode layer, and the light-emitting layer. In other embodiments, the light-emitting device may further comprise a hole-transport layer disposed between the anode and the light-emitting layer. The hole-transport layer may comprise at least one hole-transport material. Suitable hole-transport materials may include those listed above in addition to any others known to those skilled in the art. In some embodiments, the light-emitting device may further comprise an electron-transport layer disposed between the cathode and the light-emitting layer. The electron-transport layer may comprise at least one electron-transport material. Suitable electron transport materials include those listed above and any others known to those skilled in the art.

If desired, additional layers may be included in the light-emitting device. These additional layers may include an electron injection layer (EIL), a hole blocking layer (HBL), an exciton blocking layer (EBL), and/or a hole injection layer (HIL). In addition to separate layers, some of these materials may be combined into a single layer.

In some embodiments, the light-emitting device can include an electron injection layer between the cathode layer and the light emitting layer. A number of suitable electron injection materials are known to those skilled in the art. Examples of suitable material(s) that can be included in the electron injection layer include but are not limited to, an optionally substituted compound selected from the following: aluminum quinolate ($Alq_3$), 2-(4-biphenylyl)-5-(4-tert-butylphenyl)-1,3,4-oxadiazole (PBD), phenanthroline, quinoxaline, 1,3,5-tris[N-phenylbenzimidazol-z-yl]benzene (TPBI) a triazine, a metal chelate of 8-hydroxyquinoline such as tris(8-hydroxyquinoliate) aluminum, and a metal thioxinoid compound such as bis(8-quinolinethiolato) zinc. In one embodiment, the electron injection layer is aluminum quinolate ($Alq_3$), 2-(4-biphenylyl)-5-(4-tert-butylphenyl)-1,3,4-oxadiazole (PBD), phenanthroline, quinoxaline, 1,3,5-tris[N-phenylbenzimidazol-z-yl]benzene (TPBI), or a derivative or a combination thereof.

In some embodiments, the device can include a hole blocking layer, e.g., between the cathode and the light-emitting layer. Various suitable hole blocking materials that can be included in the hole blocking layer are known to those skilled in the art. Suitable hole blocking material(s) include but are not limited to, an optionally substituted compound selected from the following: bathocuproine (BCP), 3,4,5-triphenyl-1,2,4-triazole, 3,5-bis(4-tert-butyl-phenyl)-4-phenyl-[1,2,4]triazole, 2,9-dimethyl-4,7-diphenyl-1,10-phenanthroline, and 1,1-bis(4-bis(4-methylphenyl)aminophenyl)-cyclohexane.

In some embodiments, the light-emitting device can include an exciton blocking layer, e.g., between the light-emitting layer and the anode. In an embodiment, the band gap of the material(s) that comprise exciton blocking layer is large enough to substantially prevent the diffusion of excitons. A number of suitable exciton blocking materials that can be included in the exciton blocking layer are known to those skilled in the art. Examples of material(s) that can compose an exciton blocking layer include an optionally substituted compound selected from the following: aluminum quinolate ($Alq_3$), 4,4'-bis[N-(naphthyl)-N-phenyl-amino]biphenyl (α-NPD), 4,4'-N,N'-dicarbazole-biphenyl (CBP), and bathocuproine (BCP), and any other material(s) that have a large enough band gap to substantially prevent the diffusion of excitons.

In some embodiments, the light-emitting device can include a hole injection layer, e.g., between the light-emitting layer and the anode. Various suitable hole injection materials that can be included in the hole injection layer are known to those skilled in the art. Exemplary hole injection material(s) include an optionally substituted compound selected from the following: a polythiophene derivative such as poly(3,4-ethylenedioxythiophene (PEDOT)/polystyrene sulphonic acid (PSS), a benzidine derivative such as N,N,N',N'-tetraphenyl-benzidine, poly(N,N'-bis(4-butylphenyl)-N,N'-bis(phenyl) benzidine), a triphenylamine or phenylenediamine derivative such as N,N'-bis(4-methylphenyl)-N,N'-bis(phenyl)-1,4-phenylenediamine, 4,4',4"-tris(N-(naphthylen-2-yl)-N-phenylamino)triphenylamine, an oxadiazole derivative such as 1,3-bis(5-(4-diphenylamino)phenyl-1,3,4-oxadiazol-2-yl) benzene, a polyacetylene derivative such as poly(1,2-bis-benzylthio-acetylene), and a phthalocyanine metal complex derivative such as phthalocyanine copper. Hole-injection materials, while still being able to transport holes, may have a hole mobility substantially less than the hole mobility of conventional hole transport materials.

Those skilled in the art recognize that the various materials described above can be incorporated in several different layers depending on the configuration of the device. In one embodiment, the materials used in each layer are selected to result in the recombination of the holes and electrons in the light-emitting layer. An example of a device configuration that incorporates the various layers described herein is illustrated schematically in FIG. 1. The electron injection layer (EIL), electron transport layer (ETL), hole blocking layer (HBL), exciton blocking layer (EBL), hole transport layer (HTL), and hole injection layer (HIL) can be incorporated in the light-emitting device using methods known to those skilled in the art (e.g., vapor deposition).

The emissive compositions may be prepared by adapting methods known in the art for other emissive compositions. For example, the emissive compositions may be prepared by dissolving or dispersing the emissive compound in a solvent and depositing the compound on the appropriate layer of the device. The liquid may be a single phase, or may comprise one or more additional solid or liquid phases dispersed in it. The solvent may then be allowed to evaporate, or the solvent may be removed via heat or vacuum, to provide an emissive composition. If a host is present, it may be dissolved or dispersed in the solvent with the emissive device and treated as explained above. Alternatively, the compound may be added to a molten or liquid host material, which is then allowed to solidify to provide a viscous liquid or solid emissive composition.

Light-emitting devices comprising the compounds disclosed herein can be fabricated using techniques known in the art, as informed by the guidance provided herein. For example, a glass substrate can be coated with a high work functioning metal such as ITO which can act as an anode. After patterning the anode layer, a light-emitting layer that includes at least a compound disclosed herein can be deposited on the anode. The cathode layer, comprising a low work functioning metal (e.g., Mg:Ag), can then be deposited, e.g., vapor evaporated, onto the light-emitting layer. If desired, the device can also include an electron transport/injection layer, a hole blocking layer, a hole injection layer, an exciton blocking layer and/or a second light-emitting layer that can be added to the device using techniques known in the art, as informed by the guidance provided herein.

In some embodiments, the light-emitting device (e.g., OLED) is configured by a wet process such as a process that comprises at least one of spraying, spin coating, drop casting, inkjet printing, screen printing, etc. Some embodiments provide a composition which is a liquid suitable for deposition onto a substrate. The liquid may be a single phase, or may comprise one or more additional solid or liquid phases dispersed in it. The liquid typically comprises a light-emitting compound, a host material disclosed herein and a solvent.

EXAMPLES

Example 1

General Synthetic Methods

While there are many ways readily apparent (in view of the teachings provided herein) to those skilled in the art to prepare the compounds disclosed, general Scheme 1 illustrates a method that can be used to prepare a variety of compounds.

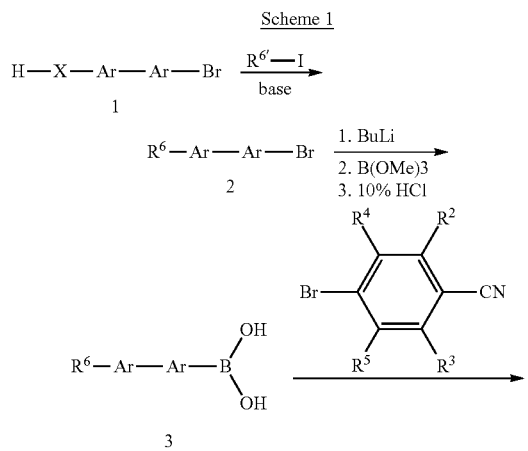

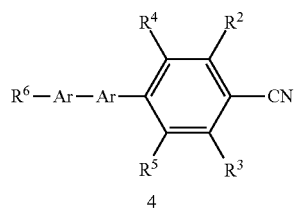

In this method, a biphenyl (compound 1) having an amine or hydroxyl moiety (—X—H) and a halogen substituent, such as Br, is coupled to $R^{6'}$—I using a catalyst such as a base (e.g. $Cs_2CO_3$) to form compound 2. The halogen, such as bromine, on the phenyl ring of compound 2 may then be then activated by a process comprising metal exchange, such as lithium exchange which may be followed by substitution with boronic acid. The compound may then be coupled to another aromatic ring (such as the one shown in the illustrated embodiment) via a second halogen-metal coupling to form compound 4, an embodiment of the compounds of Formula 1. A variety of substitution is available on the aryl rings are available via commercially available sources and/or standard chemistry.

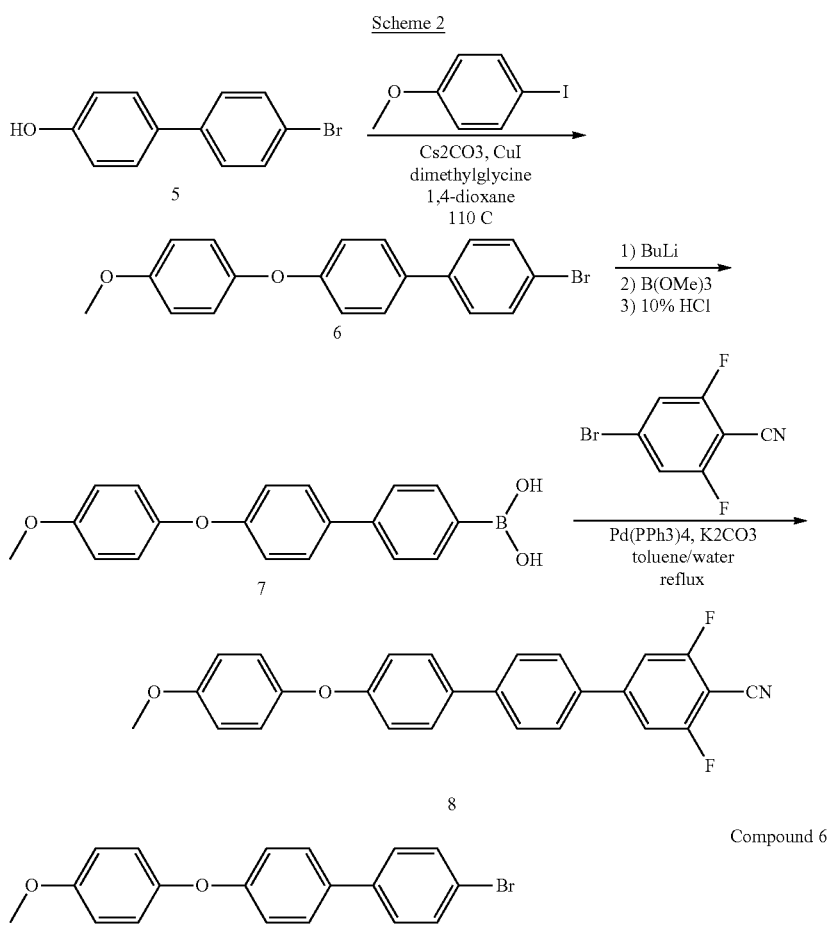

A mixture of 4'-Bromo-(1,1'-biphenyl)-4-ol (10.0 g, 40.1 mmol), 4-iodoanisole (18.72 g, 80.0 mmol), cesium carbonate (26.1 g, 80.2 mmol), copper iodide (760 mg, 4.0 mmol), dimethylglycine hydrochloride (1.68 g, 12.0 mmol), and anhydrous 1,4-dioxane (50 mL) was purged via freeze-pump-thaw method. The mixture was then heated to 110° C. overnight. After cooling, mixture was poured into ethyl acetate (300 mL), and stirred at 40° C. for 30 min. The solids were filtered, and the filtrate was dried under vacuum to give ivory solids. These solids were washed with a mixture of ethyl acetate and methanol to give pure compound 6 product; 6.5 g, 46% yield; confirmed by $^1$H NMR Compound 7

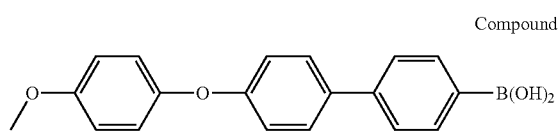

Compound 6 (2.0 g, 5.63 mmol) was dissolved in anhydrous tetrahydrofuran (30 mL), and the solution was cooled to −78° C. Butyllithium (3.43 mL of a 1.6 M solution, 5.5 mmol) was added dropwise to the solution and the resulting mixture was stirred at −78° C. for three hours. Trimethyl borate (0.572 mL, 5.5 mmol) was then added slowly, and mixture was stirred for three hours at room temperature. Saturated ammonium chloride solution (45 mL) (alternatively, 10% HCl solution) was added and the mixture was stirred overnight at room temperature. The product was then extracted with ethyl acetate (2×100 mL) and the organic layer was dried under vacuum. Precipitation of the solutes in methylene chloride/methanol gave white solids. White solids were filtered and washed with methanol. The filtrate was dried to give relatively pure compound 7 product; 1.2 g, 53% yield; relatively pure by $^1$H NMR.

Compound 8

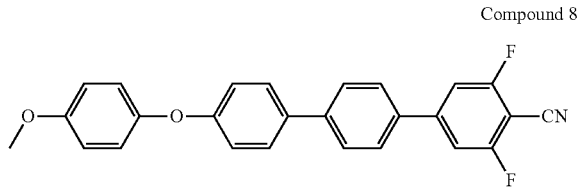 [SMILES: COc1ccc(Oc2ccc(-c3ccc(-c4cc(F)c(C#N)c(F)c4)cc3)cc2)cc1]

A mixture of compound 7 (100 mg, 0.297 mmol), 2,6-difluorobenzenonitrile (67 mg, 0.310 mmol), tetrakis(triphenylphosphine)palladium (35 mg, 0.03 mmol), potassium carbonate (83 mg, 0.6 mmol), toluene (10 mL), and water (2 mL) was degassed, and heated to reflux (130° C.) overnight. After cooling, the mixture was poured into ethyl acetate, the solids were filtered off and the filtrate was washed with water and dried with sodium sulfate. The organic layer was then loaded onto silica gel, and purification by silica gel column (gradient of 30:1 to 6:1 hexanes:ethyl acetate) gave 48 mg of compound 8 product (40% yield); pure by $^1$H NMR.

Example 2

Device Fabrication

Fabrication of light-emitting device: ITO-coated glass substrates were cleaned by ultrasound in acetone, and consecutively in 2-propanol, baked at 110° C. for about 3 hours, followed by treatment with oxygen plasma for about 5 min. A layer of PEDOT: PSS (Baytron P purchased from H.C. Starck) was spin-coated at about 3000 rpm onto the pre-cleaned and $O_2$-plasma treated (ITO)-substrate and annealed at about 180° C. for about 10 min, yielding a thickness of about 40 nm. In a glove-box hosted vacuum deposition system at a pressure of $10^{-7}$ torr (1 torr=133.322 Pa), 4,4'4"-tri(N-carbazolyl)triphenylamine (TCTA) was first deposited on top of the PEDOT/PSS layer at a deposition rate of about 0.06 nm/s, yielding about a 30 nm thick film. Then 4,4'-bis(carbazol-9-yl)biphenyl (CBP) and deep blue emitter compound 8 were concurrently heated and deposited on top of the TCTA at a different deposition speed to make the 8 layer at about 3 wt % (about 0.0018 nm/s), followed by deposition of 1,3,5-tris(N-phenylbenzimidizol-2-yl)benzene (TPBI) at a deposition rate of about 0.06 nm/s. CsF and Al were then deposited successively at deposition rates of about 0.005 nm/s and about 0.2 nm/s, respectively. Each individual device had areas of about 0.14 cm$^2$.

Example 3

Device Performance

Device A, comprising Compound 8 and fabricated in accordance with Examples 1 and 2, was tested to determine the emissive qualities of the device by examining the (1) emissive intensity of Device A (intensity of the device [a.u.] as a function of wavelength; (2) determining the CIE coordinates of Device A; and (3) determining the efficiency of Device A (current density and luminescence as a function of the voltage applied to the device; and external quantum efficiency and luminescence as a function of current density). All spectra were measured with an Ocean Optics HR 4000 spectrometer (Ocean Optics, Dunedin, Fla., USA) and I-V-L characteristics were taken with a Keithley 2400 SourceMeter (Keithley Instruments, Inc., Cleveland, Ohio, USA) and Newport 2832-C power meter and 818 UV detector (Newport, Corp., Irvine, Calif., USA). All device operation was performed inside a nitrogen-filled glove-box. An exemplary configuration of the device (Device A) is shown in FIG. 1.

Figure 2:
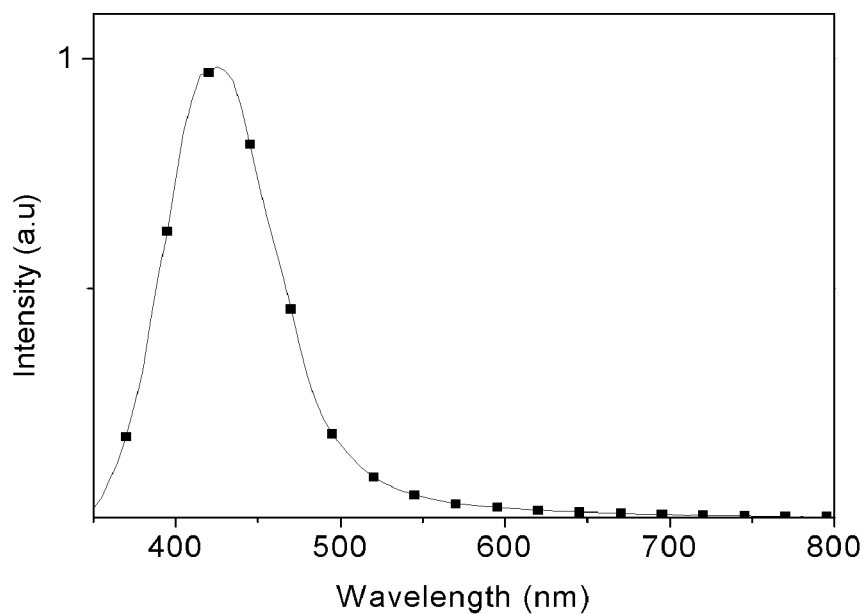
FIG. 2 is graph depicting the electroluminescent spectrum (intensity (a.u.) as a function of wavelength) and CIE coordinates of an embodiment of a device of FIG. 1.

FIG. 2 shows electroluminescence spectrum of Device A, plus the CIE coordinate. The spectrum shows significant emission between about 400 and about 500 nm. The purity of the deep blue emitted radiation is demonstrated by the CIE coordinates (X=0.16; Y=0.10).

Figure 3:
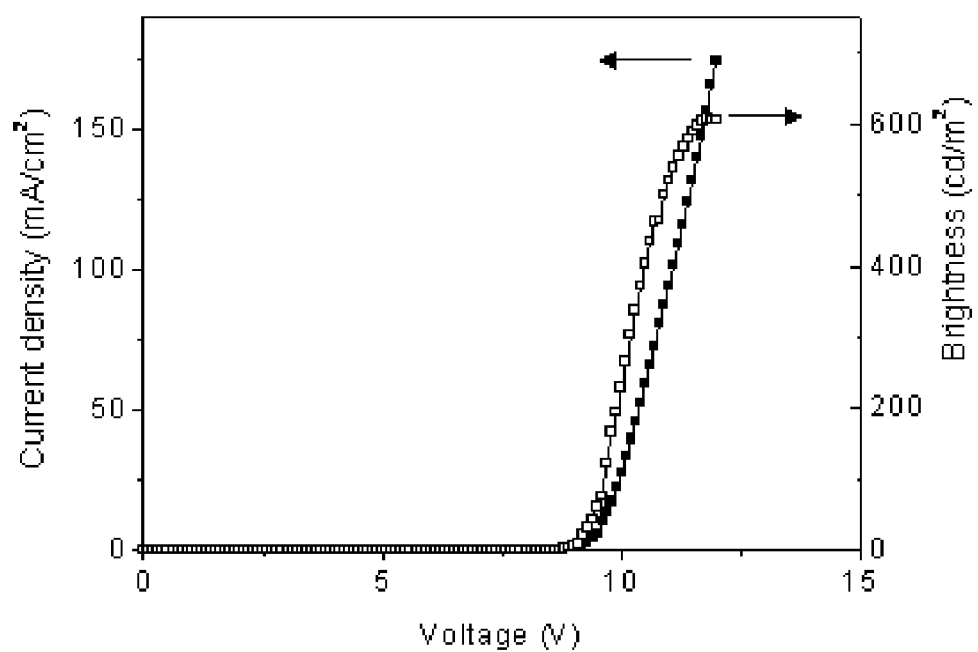
FIG. 3 is a graph depicting the Current density ($mA/cm^2$) and luminance ($cd/m$) as a function of the driving voltage (volts) of an embodiment of a device of FIG. 1.
Figure 4:
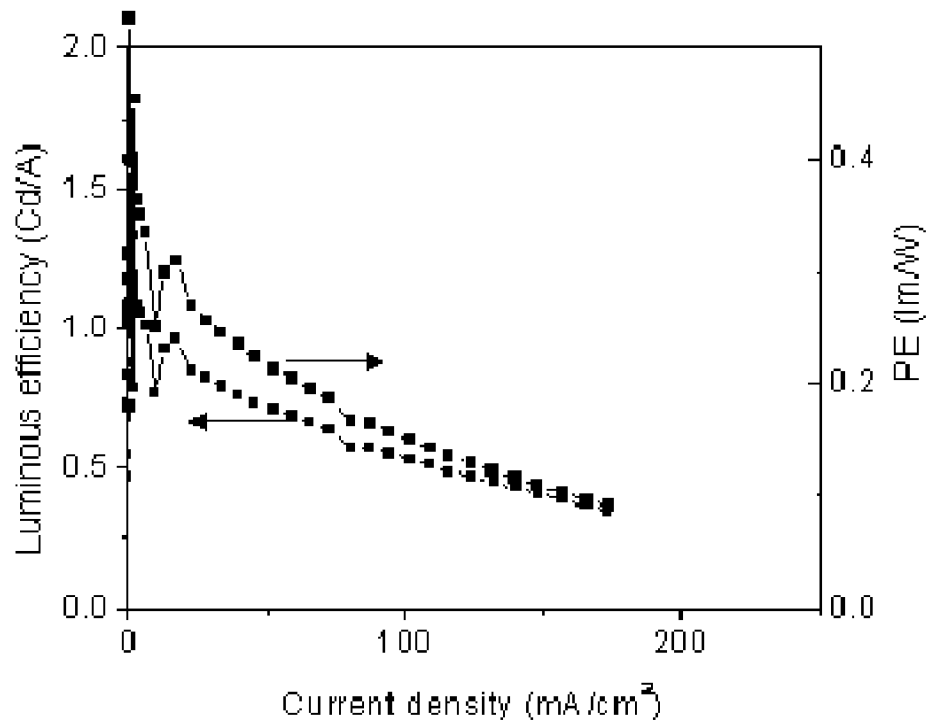
FIG. 4 is a graph depicting the luminous efficiency and External Quantum Efficiency (EQE (%)) as a function of current density of an embodiment of a device of FIG. 1.
Figure 4:
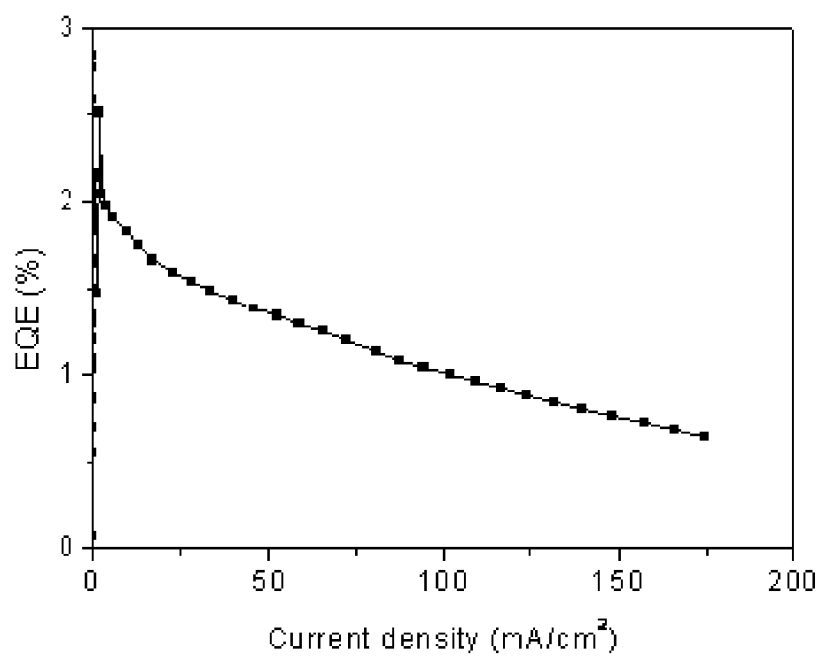

In addition, as shown in FIGS. 3 and 4, Device A demonstrates efficacy in conventional LED operating parameters. FIG. 3 demonstrates that the Current density (mA/cm2) and luminance (cd/m) as a function of the driving voltage (volts) of Device A are within acceptable ranges for light emitting diodes.

FIG. 4 demonstrates that the luminous efficiency and External Quantum Efficiency (EQE [%]) as a function of current density of Device A are within acceptable ranges for light emitting diodes. Thus Compound 8 has demonstrated its effectiveness as a blue emitting compound in light emitting devices, indicating that other compounds of the Formula 1 are likely to perform similarly.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A compound represented by a formula:

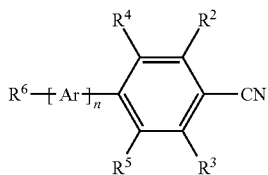

wherein $R^2$ and $R^3$ are independently F, Cl, or $C_{1-12}$ perflouroalkyl;

$R^4$ and $R^5$ are independently H, F, Cl, or $C_{1-10}$ alkyl;

each Ar is independently 1,4-interarylene having 0, 1, or 2 substituents independently selected from $C_{1-3}$ alkyl, F, and Cl;

n is 1, 2, or 3, $R^6$ is an optionally substituted diarylamino, optionally substituted diarylaminophenoxy, or $R^7$—O-Ph-O—;

Ph is optionally substituted p-interphenylene; and $R^7$ is $C_{1-10}$ alkyl or $C_{1-9}O_{1-4}$ ether.

2. The compound of claim 1, wherein $R^2$ and $R^3$ are independently F or Cl.

3. The compound of claim 2, wherein $R^2$ and $R^3$ are F.

4. The compound of claim 3, wherein n is 2.

5. The compound of claim 4, wherein $R^7$ is $C_{1-4}$ alkyl.

6. The compound of claim 4 wherein $R^6$ is:

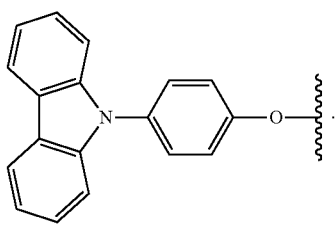 [SMILES: *Oc1ccc(-n2c3ccccc3c3ccccc32)cc1 ; "."]

7. The compound of claim 4 wherein $R^6$ is:

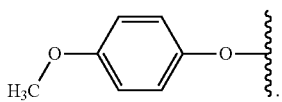

8. The compound of claim 1, wherein at least one Ar is unsubstituted.

9. The compound of claim 1, further represented by a formula:

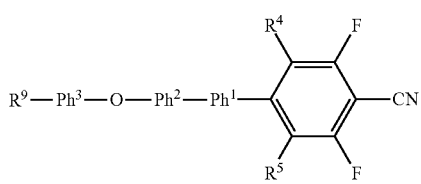

(Formula 2)

or

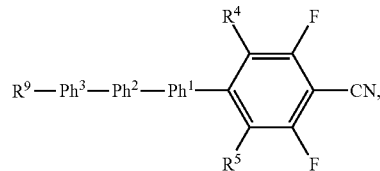

(Formula 3)

wherein $Ph^1$, $Ph^2$, and $Ph^3$ are independently p-interphenylene having 0, 1, or 2 substituents independently selected from $C_{1-3}$ alkyl, F, and Cl; and $R^9$ is O—$R^7$ in Formula 2 and $R^9$ is optionally substituted carbazol-9-yl in Formula 3.

10. The compound of claim 9, further represented by a formula:

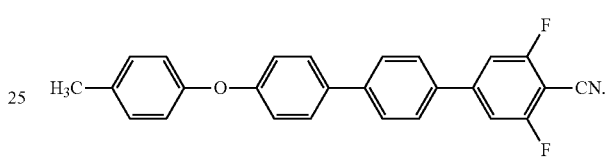

11. The compound of claim 9, further represented by a formula:

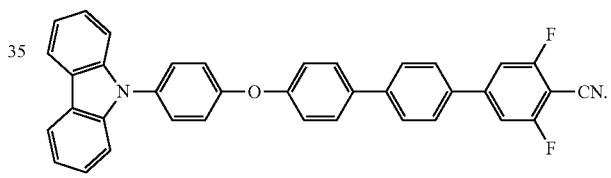

12. The compound of claim 9, further represented by a formula:

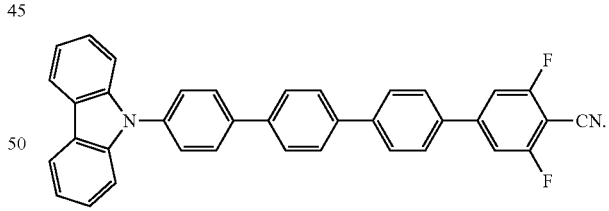

13. A light-emitting device, comprising:

an anode layer;

a cathode layer; and a light-emitting layer positioned between the anode layer and the cathode layer, the light-emitting layer comprising a compound according to claim 1.

14. The device of claim 13, wherein $R^2$ and $R^3$ are independently F or Cl.

15. The device of claim 13, wherein n is 2.

16. The device of claim 13, wherein $R^7$ is $C_{1-4}$ alkyl.

17. The device of claim 13 wherein $R^6$ is:

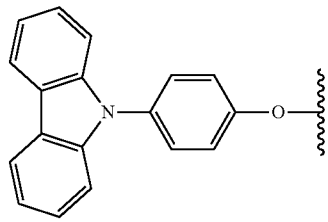

or

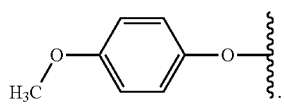

18. The device of claim 13, wherein at least one Ar is unsubstituted.

19. The device of claim 13, wherein the compound is further represented by a formula:

(Formula 2)

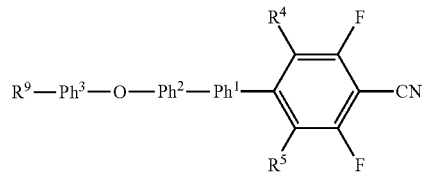

or (Formula 3)

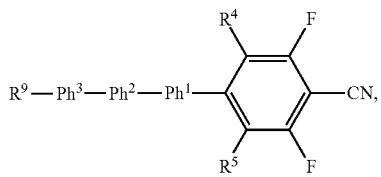

wherein $Ph^1$, $Ph^2$, and $Ph^3$ are independently p-interphenylene having 0, 1, or 2 substituents independently selected from $C_{1-3}$ alkyl, F, and Cl; and
$R^9$ is $O-R^7$ in Formula 2 and $R^9$ is optionally substituted carbazol-9-yl in Formula 3.

20. The device of claim 13, wherein the compound is selected from the group consisting of:

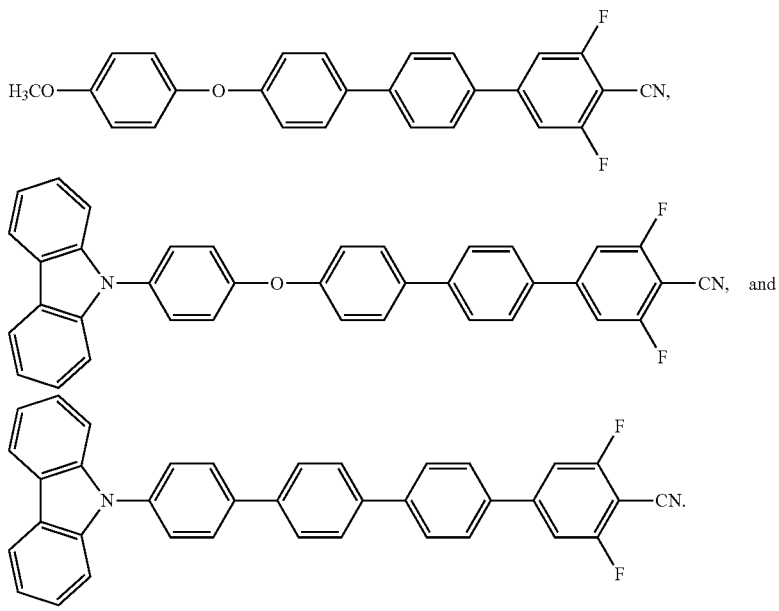

* * * * *